United States Patent
Etinger et al.

(10) Patent No.: US 7,098,342 B2
(45) Date of Patent: Aug. 29, 2006

(54) PREPARATION OF CANDESARTAN CILEXETIL

(75) Inventors: Marina Yu Etinger, Nesher (IL); Boris Fedotev, Haifa (IL); Ben-Zion Dolitzky, Petach Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 87 days.

(21) Appl. No.: 10/968,710

(22) Filed: Oct. 18, 2004

(65) Prior Publication Data

US 2005/0131037 A1    Jun. 16, 2005

Related U.S. Application Data

(60) Provisional application No. 60/568,649, filed on May 5, 2004, provisional application No. 60/537,995, filed on Jan. 21, 2004, provisional application No. 60/523,524, filed on Nov. 18, 2003, provisional application No. 60/512,566, filed on Oct. 16, 2003.

(51) Int. Cl.
  *C07D 403/08*    (2006.01)
  *C07D 257/04*    (2006.01)
(52) U.S. Cl. ...................... 548/250; 548/252
(58) Field of Classification Search ............... 548/250, 548/252
  See application file for complete search history.

(56) References Cited

U.S. PATENT DOCUMENTS

| 5,196,444 | A | 3/1993 | Naka et al. |
| 5,385,925 | A | 1/1995 | Narr et al. |
| 5,578,733 | A | 11/1996 | Shida et al. |
| 5,587,393 | A | 12/1996 | Narr et al. |
| 5,684,029 | A | 11/1997 | Narr et al. |
| 5,763,619 | A | 6/1998 | Shida et al. |
| 5,962,491 | A | 10/1999 | Naka et al. |
| 2002/0151723 | A1 | 10/2002 | Takehiko et al. |
| 2004/0215023 | A1 | 10/2004 | Hashimoto et al. |

FOREIGN PATENT DOCUMENTS

| EP | 0 425 921 A | 5/1991 |
| EP | 0 459 136 A | 12/1991 |
| EP | 0 881 212 A | 12/1998 |
| EP | 1 420 016 A | 5/2004 |

OTHER PUBLICATIONS

Matsunaga, et al.: "Solid-State Characterization of Candesartan Colexetil (TCV-116): Crystal Structure and Molecular Mobiluty", Chem. Pharm. Bull. 47 (2), pp. 182-186 (1999).

*Primary Examiner*—Taofiq Solola
(74) *Attorney, Agent, or Firm*—Kenyon & Kenyon LLP

(57) ABSTRACT

The invention encompasses processes for the synthesis of cilexetil trityl candesartan from the reaction of trityl candesartan with cilexetil halide in the presence of a base and a low boiling organic solvent. Optionally, the reaction may be conducted in the presence of a phase transfer catalyst.

24 Claims, No Drawings

PREPARATION OF CANDESARTAN CILEXETIL

RELATED APPLICATIONS

This application claims the benefit of U.S. Provisional Application Nos. 60/512,566, filed on Oct. 16, 2003; 60/523,524, filed on Nov. 18, 2003; 60/537,995, filed on Jan. 21, 2004; and 60/568,649, filed on May 5, 2004.

FIELD OF THE INVENTION

The present invention encompasses preparation of candesartan trityl cilexetil. The present invention also encompasses preparation of candesartan cilexetil by the deprotection of cilexetil trityl candesartan (TCC) using at least one organic solvent and/or at least one organic acid. The present invention encompasses crystallizing and recrystallizing the candesartan cilexetil.

BACKGROUND OF THE INVENTION

Candesartan is a potent, long-acting, selective $AT_1$ subtype angiotensin II receptor antagonist. Candesartan meets the requirement of high potency but it is poorly absorbed by the body when administered orally. To overcome the poor absorption, the prodrug candesartan cilexetil was developed. During absorption in the gastrointestinal tract candesartan cilexetil is rapidly and completely hydrolyzed to candesartan. The chemical name for candesartan is: 2-ethoxy-1-[[2'-(1H-tetrazol-5-yl)biphenyl-4-yl]methyl]-1H-benzimidazole-7-carboxylic acid. The chemical name for candesartan cilexetil is (±)-1-[[(cyclohexyloxy)carbonyl]oxy]ethyl-2-ethoxy-1-[[2'-(1H-tetrazol-5-yl) 1,1'biphenyl-4-yl]methyl]-1H-benzimidazole-7-carboxylate. Candesartan cilexetil is a white to off-white powder and is sparingly soluble in water and in methanol. Although candesartan cilexetil contains an asymmetric center in the ester portion of the molecule, candesartan cilexetil is sold as the racemic mixture.

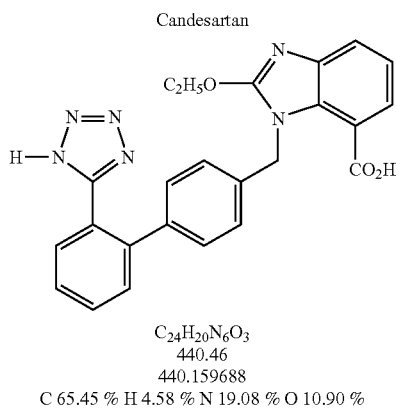

Candesartan $C_{24}H_{20}N_6O_3$
440.46
440.159688
C 65.45 % H 4.58 % N 19.08 % O 10.90 %

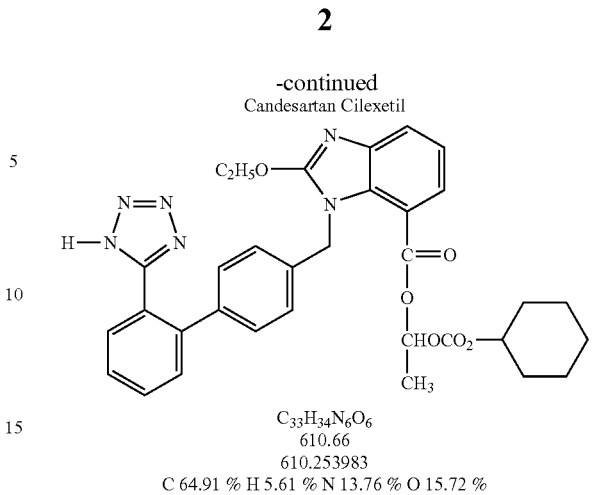

-continued
Candesartan Cilexetil $C_{33}H_{34}N_6O_6$
610.66
610.253983
C 64.91 % H 5.61 % N 13.76 % O 15.72 %

Angiotensin II is formed from angiotensin I in a reaction catalyzed by angiotensin-converting enzyme (ACE, kininase II). Angiotensin II is the principal pressor agent of the renin-angiotensin system, with effects that include vasoconstriction, stimulation of synthesis and release of aldosterone, cardiac stimulation, and renal reabsorption of sodium. Angiotensin II helps maintain constant blood pressure despite fluctuations in a person's state of hydration, sodium intake and other physiological variables. Angiotensin II also performs regulatory tasks such as inhibiting excretion of sodium by the kidneys, inhibiting norephedrin reuptake, and stimulating aldosterone biosynthesis. Candesartan blocks the vasoconstrictor and aldosterone secreting effects of angiotensin II by selectively blocking the binding of angiotensin II to the $AT_1$ receptor in many tissues, such as vascular smooth muscle and the adrenal gland. By inhibiting angiotensin II binding to $AT_1$ receptors, candesartan disrupts the vasoconstriction mediated by $AT_1$ receptors. Blocking vasoconstriction by angiotensin II has been found to be beneficial to patients with hypertension. The United States Food and Drug Administration has approved candesartan for the treatment of hypertension alone or in combination with other antihypertensive agents.

U.S. Pat. No. 5,196,444 discloses working Example 7, 1-[[(cyclohexyloxy)carbonyl]oxy]ethyl-2-ethoxy-1-[[2'-(1H-tetrazol-5-yl) 1,1'biphenyl-4-yl]methyl]-1H-benzimidazole-7-carboxylate was formed by reacting 2-ethoxy-1-[[2'-(N-triphenylmethyltetrazol-5-yl)biphenyl-4-yl]methyl]benzimidazole-7-carboxylic acid in DMF with cyclohexyl-1-iodoethyl carbonate to form cilexetil trityl candesartan and deprotecting with a methanolic hydrochloric acid to form candesartan cilexetil.

U.S. Pat. No. 5,578,733, discloses the deprotection of cilexetil trityl candesartan using mineral acids under substantially anhydrous conditions.

SUMMARY OF THE INVENTION

One embodiment of the invention encompasses processes for preparing cilexetil trityl candesartan comprising reacting trityl candesartan, cilexetil halide and at least one base in a low boiling organic solvent to form cilexetil trityl candesartan; and isolating cilexetil trityl candesartan. The process may further comprise adding at least one phase transfer catalyst.

In a preferred embodiment of the invention, in the process for preparing cilexetil trityl candesartan, the low boiling organic solvent has a boiling point of less than about 140° C.

Process for preparing cilexetil candesartan comprises the step of preparing cilexetil trityl candesartan comprising reacting trityl candesartan, cilexetil halide and at least one base in a low boiling organic solvent to form cilexetil trityl candesartan.

Another embodiment of the invention encompasses methods of synthesizing cilexetil candesartan comprising providing cilexetil trityl candesartan; reacting cilexetil trityl candesartan with at least one organic acid to form cilexetil candesartan in at least one organic solvent; and isolating the crude cilexetil candesartan.

One embodiment of the invention encompasses method for synthesizing cilexetil candesartan comprising providing cilexetil trityl candesartan; mixing cilexetil trityl candesartan in the presence of methanol without an acid; and isolating the crude cilexetil candesartan.

Another embodiment of the invention encompasses crystallizing the crude candesartan cilexetil using a solvent system having at least two solvents to obtain a crystalline candesartan cilexetil; and recrystallizing the crystalline candesartan cilexetil.

DETAILED DESCRIPTION OF THE INVENTION

One embodiment of the invention encompasses processes for the synthesis of cilexetil trityl candesartan from the reaction of trityl candesartan with cilexetil halide in the presence of a base and a low boiling organic solvent. Optionally, the reaction may be conducted in the presence of a phase transfer catalyst. Preferably, the cilexetile halide is cilexetil chloride. Another embodiment of the invention encompasses methods of deprotecting cilexetil trityl candesartan into cilexetil candesartan using at least one organic acid in the presence of a substantially dry organic solvent, optionally with addition of water. Another embodiment of the invention encompasses methods of deprotecting cilexetil trityl candesartan into cilexetil candesartan using at least one inorganic acid in the presence of an aqueous solvent. Another embodiment of the invention encompasses methods of deprotecting cilexetil trityl candesartan into cilexetil candesartan in the presence of methanol without an acid. Optionally, the process may further comprise the crystallization and recrystallization of cilexetil candesartan.

Typically, the process for the synthesis of cilexetil trityl candesartan comprises reacting trityl candesartan, cilexetil halide, and at least one base in a low boiling organic solvent for a sufficient time and at a sufficient temperature and isolating cilexetil trityl candesartan. Preferably, the cilexetil halide is cilexetil chloride. The process advantageously uses a low boiling point organic solvent which is easier to remove from the product mixture and environmentally safer than solvents previously used in the synthesis. Not to be limited by theory, however, it is believed that in some of the processes of the invention, the base may be insoluble in the low boiling organic solvent and a two-phase system may be formed. Because the reaction may occur at the interface between the two phases, the rate of such an interfacial reaction may be greatly increased by use of a phase transfer catalyst (PTC).

The solvents used in the process are solvents with a low boiling point. Typically, a low boiling organic solvent has a boiling point of less than about 140° C. and preferably a boiling point of less than about 120° C. Alternatively, the low boiling organic solvent is a pharmaceutically acceptable low boiling point organic solvent having a boiling point from about 140° C. to about 70° C., and preferably a boiling point from about 120° C. to about 80° C. Typically, the solvents include, but are not limited to, at least one of hydrocarbon aliphatic solvents, aromatic solvents, or ethers. In a preferred embodiment, one solvent may be acetonitrile, which has a boiling point of 81° C. to 82° C., or toluene, which has a boiling point of 110° C. In contrast, the solvents used in the prior art, such as dimethylforamide, has a boiling point of 153° C. However, if DMF is used in the reaction of the invention, then the reaction temperature may be from about 50° C. to about 55° C. and not the reflux temperature.

The base in the reaction may be at least one of an inorganic base or an organic base. Inorganic bases used in the reaction include, but are not limited to, lithium hydroxide, sodium hydroxide, potassium hydroxide, cesium hydroxide, lithium carbonate, sodium carbonate, potassium carbonate, cesium carbonate, lithium hydrogen carbonate, sodium hydrogen carbonate, potassium hydrogen carbonate, and silver carbonate. Organic bases used in the reaction include, but are not limited to, triethylamine, diisopropylethylamine, pyridine, N,N-dimethylaniline, N-methyl-morpholine, 4-dimethylaminopyridine, 1,5-diazabicyclo-[4.3.0]non-5-ene (DBN), 1,8-diazabicyclo[5.4.0]undec-7-ene (DBU), or 1,4-diazabicyclo[2.2.2]octane (DABCO). Preferably, the base is potassium carbonate.

Several classes of compounds are known to be capable of acting as phase transfer catalysts, for example quaternary ammonium compounds and phosphonium compounds, to mention just two. Phase transfer catalysts include, but are not limited to, at least one of tetrabutylammonium bromide, TEBA, tetrabutylammonium hydrogensulfate, tricaprylylmethylammonium chloride, benzyltriethylammonium chloride, cetyltrimethylammonium bromide, cetylpyridinium bromide, N-benzylquininium chloride, tetra-n-butylammonium chloride, tetra-n-butylammonium hydroxide, tetra-n-butylammonium iodide, tetra-ethylammonium chloride, benzyltributylammonium bromide, benzyltriethylammonium bromide, hexadecyltriethylammonium chloride, tetramethylammonium chloride, hexadecyltrimethyl ammonium chloride, or octyltrimethylammonium chloride. Preferably, the phase transfer catalyst includes, but is not limited to, at least one of tetrabutylammonium bromide, TEBA, tricaprylylmethylammonium chloride, or tetrabutylammonium hydrogensulfate. The phase transfer catalysts are either commercially available or readily synthesized by one of ordinary skill in the art. For example tricaprylylmethylammonium chloride, commonly know as Aliquat® 336, is manufactured by Aldrich Chemical Company, Inc. Milwaukee, Wis.

The lower boiling point organic solvent used in the reaction allows for lower reaction temperatures for the synthesis of cilexetil trityl candesartan. Based on the low boiling solvent. Typically, the reaction temperature is from about 25° C. to about 110° C., and preferably from about 40° C. to about 90° C. The reaction time will depend upon the amount of reactants, reaction temperature, and other variables commonly known to one of ordinary skill in the art.

Another embodiment of the invention encompasses methods for the deprotection of cilexetil trityl candesartan (I) using a mixture of at least one organic solvent and at least one organic acid to form crude cilexetil candesartan (II). In another embodiment, the organic solvent may be substantially dry organic solvent. Yet, in another embodiment, the methods include a mineral acid in addition to the organic acid. Another embodiment of the invention encompasses neutralizing the excess acid in the reaction mixture with at least one base, after adding the organic solvent. Not to be limited by theory, however, it is believed that the organic acid is easily removed from the reaction mixture during regular work-up. Accordingly, as a general matter, organic acids are easier to be used in an industrial scale. The present invention uses an organic solvent with at least one organic acid to deprotect the cilexetil trityl candesartan. As used herein, the term "substantially dry organic solvent" refers to an organic solvent having less than about 3% water by weight, and preferably less than about 0.5% water by weight.

The method encompasses deprotecting cilexetil trityl candesartan comprising: mixing cilexetil trityl candesartan and at least one organic acid in at least one organic solvent for a suitable time and at a suitable temperature to synthesize cilexetil candesartan; and isolating the crude cilexetil candesartan. The deprotecting step is depicted in Scheme I.

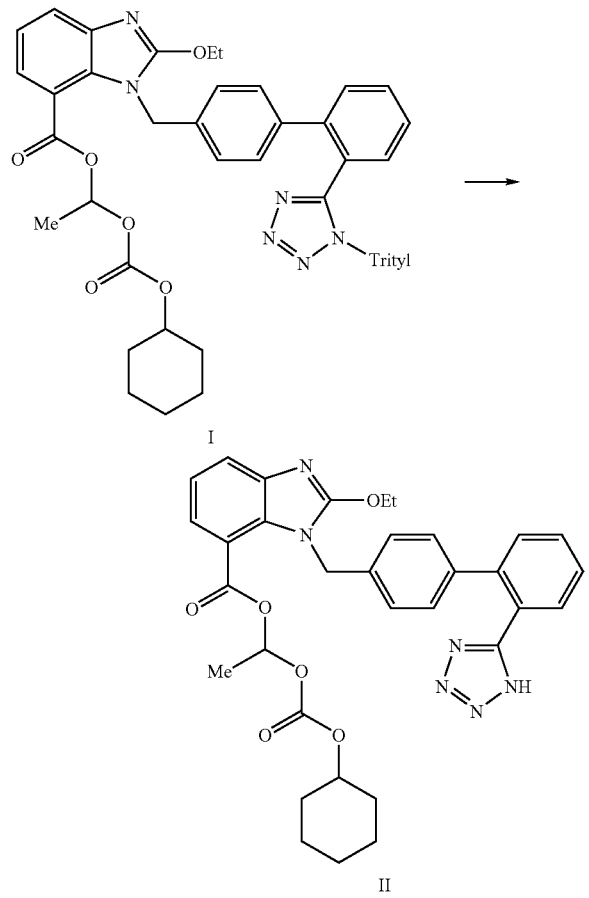

Organic acids contemplated for the method of the invention include, but are not limited to, at least one of $C_6$–$C_{10}$ aromatic sulfonic acids, haloacetic acids, $C_1$–$C_6$ alkyl sulfonic acids, or $C_1$–$C_6$ carboxylic acids. Preferably, the organic acids include, but are not limited to, at least one of methanesulfonic acid, formic acid, pyridine p-toluene sulphonic acid, trifluoroacetic acid, trichloroacetic acid, or acetic acid. Preferably, when using an organic acid, the reaction temperature may be from about 15° C. to about 60° C. Reaction time may easily be determined by monitoring the reaction progress and/or completion by thin layer chromatography (TLC). Typical reactions times may be from about 4 hours to about 20 hours.

Organic solvents include, but are not limited to, at least one alcohol, ketone, ether, hydrocarbon, or chlorinated solvent. Preferably, organic solvents include at least one $C_1$–$C_4$ alkyl alcohol, ketone, ether, or chlorinated solvent. In particular, organic solvents include, but are not limited to, dichloromethane, methanol, toluene, or tert-butyl methyl ether. In one embodiment, wherein more than one solvent is used, the ratio of first to second solvents is from about 1:10 to about 10:1.

After the trityl group has been removed, the reaction mixture is neutralized using a base. Bases include those enumerate above, and preferably, the base is NaOH. The isolation of the cilexetil candesartan can be carried out by extraction, evaporation, crystallization, or other techniques commonly used to isolate an organic compound of interest from a reaction mixture. In a preferred embodiment, the solvent may be evaporated under reduced pressure, and thereafter, the residue is diluted with water and extracted with a suitable organic solvent, such as ethyl acetate. The organic extracts are combined, dried, and the solvent removed to obtain crude compound II.

One embodiment of the invention encompasses deprotecting cilexetil trityl candesartan comprising: mixing cilexetil trityl candesartan in the presence of methanol without an acid; and isolating the cilexetil candesartan. The deprotecting step of the trityl group can be performed in presence of water. The deprotecting step of the trityl group can be performed in presence of organic solvent to facilitate the precipitation of the compound at the end of the reaction. This deprotection process comparatively yields a clean product.

Typically, the deprotection step comprises heating to reflux trityl candesartan cilexetil in methanol. Optionally, the deprotection solvent mixture further comprises an organic solvent, such as toluene, and/or an acid, such as formic acid. The cilexetil trityl candesartan is heated to reflux until a clear solution is obtained. Typically, the reaction temperature is from about 30° C. to about 90° C., preferably from about 50° C. to about 90° C., and the heating takes place for about 5 to about 19 hours, preferably for about 8 to about 12 hours. Thereafter, the solvents are removed by evaporation to obtain crude deprotected candesartan cilexetil. The solvents may be removed at a temperature of about 30° C. to about 70° C., preferably at a temperature of about 50° C., and at a reduce pressure of about 30 mbar.

As used herein, the term "crude" refers to the product obtained from the deprotection reaction. The crude candesartan cilexetil may be either a solid form or an oil form.

Typically, crude candesartan cilexetil is dissolved in a minimal amount of the solvent system, thereafter the solution is cooled slowly until a crystalline candesartan cilexetil precipitate appears. Crystallization may be induced by seeding, etching, cooling, or other techniques commonly known to one of ordinary skill in the art. Optionally, during the crystallization step, the solution may be stirred. Thereafter, the crystalline candesartan cilexetil obtained during the first crystallization is allowed to dry. The drying step may be performed by heating the crystalline candesartan cilexetil, optionally under reduced pressure, until a constant weight is obtained. Typically, drying is performed at a temperature of about 45° C. to about 65° C., and preferably at a temperature of about 50° C. to about 60° C. When present, the reduce pressure, includes, but is not limited to, about 30 mbar.

The solvent system comprises at least two solvents, wherein one solvent is an alcohol and another solvent is an aromatic compound. Typically, the alcohol is at least one $C_1$–$C_6$ alcohol including, but not limited to, methanol, ethanol, propanol, isopropanol, butanol, sec-butanol, tert-butanol, 1-pentanol, 2-pentanol, or 3-pentanol. Preferably, the alcohol is methanol. The aromatic compound is at least one compound with a phenyl ring including, but not limited to, substituted or unsubstituted benzene, toluene, ethyltoluene, xylene, or mesitylene. Preferably, the aromatic compound is toluene. Generally, the solvent system comprises an alcohol and aromatic compound in a ratio of about 20% alcohol to 80% aromatic by weight; preferably, the ratio of alcohol to aromatic compound is about 10% alcohol to 90% aromatic by weight of the solvent mixture. More preferably, the weight ratio of alcohol to aromatic compound is about 5% alcohol to 95% aromatic by weight.

The recrystallizing of crystalline candesartan cilexetil comprises dissolving the crystalline candesartan cilexetil in a solvent and recrystallizing to obtain a substantially pure candesartan cilexetil. Optionally, during the recrystallization, the solution may be stirred. Typically, the solvent comprises at least one $C_1$–$C_6$ alcohol including, but not limited to, methanol, ethanol, propanol, isopropanol, butanol, sec-butanol, tert-butanol, 1-pentanol, 2-pentanol, or 3-pentanol. Preferably, the alcohol is methanol.

Optionally, the process may further comprise a drying step wherein after the second recrystallization, the substantially pure candesartan cilexetil is dried at a suitable temperature and for a suitable time to obtain a substantially pure dry candesartan cilexetil of a constant weight. Generally, the drying temperature should be sufficient to remove undesired solvents until the weight of the crystalline candesartan cilexetil does not fluctuate. For example, the drying temperature may be about 50° C. to 65° C., and preferably, the drying temperature is about 50° C. Optionally, the drying step may be performed at a reduced pressure including, but not limited to, about 8 mbar.

Having described the invention with reference to certain preferred embodiments, other embodiments will become apparent to one skilled in the art from consideration of the specification. The invention is further defined by reference to the following examples describing in detail the preparation of the composition and methods of deprotection of the invention. It will be apparent to those skilled in the art that many modifications, both to materials and methods, may be practiced without departing from the scope of the invention.

EXAMPLES

Example 1

Method of Making Cilexetil Trityl Candesartan in a Low Boiling Solvent

A suspension of trityl candesartan (2.0 g, 2.93 mmol), cilexetil chloride (1.21 g, 5.86 mmol), potassium carbonate (0.81 g, 5.86 mmol) and acetonitrile (19 g) was stirred at 40° C. for about 8 h, and the reaction was monitored by TLC. The acetonitrile was removed at 30° C. to 35° C. under reduced pressure (10 mbar), and the residue was mixed with water (20 ml) and ethyl acetate (30 ml). The water layer was separated and extracted with ethyl acetate (20 ml×2). The combined organic layers were washed with brine (10 ml×2), dried over sodium sulfate, and evaporated to give cilexetil trityl candesartan crude, as a semi-solid, 94.38% pure by HPLC.

The crude product was triturated with hexane (30 ml) at 25° C. to 27° C. for about 3 h. Thereafter, the solids were filtered off, washed on the filter with hexane (5 g×2) and dried at 25° C. to 27° C. under reduced pressure (10 mbar) to give cilexetil trityl candesartan (12 g, 84.8%) 94.64% pure by HPLC.

Example 2

Method of Making Cilexetil Trityl Candesartan With a PTC

A suspension of trityl candesartan (2.0 g, 2.93 mmol), cilexetil chloride (1.21 g, 5.86 mmol), potassium carbonate (1.22 g, 8.83 mmol), and tetrabutylammoniumhydrogensulfate (0.2 g) in toluene (20 ml) was stirred at 50° C. to 55° C. for about 8.5 h. The reaction progress was monitored by TLC. The mixture was poured into water (100 ml) and neutralized with citric acid (solid). The organic layer was separated, washed with water, and extracted with ethyl acetate (20 ml×3). The combined organic layers were washed with brine (10 ml), dried over sodium sulfate, and evaporated. The residue was triturated with hexane (20 ml) at 20–25° C. for about 30 min, filtered and dried at 40° C. and at less than about 30 mbar to give white powder (1.68 gr, 67.2%), with 97.90% purity by HPLC.

Example 3

Method of Deprotection Using Methanesulfonic Acid

A solution of cilexetil trityl candesartan (0.50 g, 0.59 mmol), methanesulfonic acid (0.09 g, 0.88 mmol), dichloromethane (10 ml) and methanol (1 ml) was stirred at 25° C. to 27° C. for about 4 h. The reaction was monitored using thin layer chromatography (TLC monitoring). The reaction mixture was neutralized with a saturated solution of sodium bicarbonate and the dichloromethane was removed under reduced pressure. The residue was diluted with water (10 ml) and extracted with ethyl acetate (20 ml×2). The combined organic layers were washed with brine (10 ml×2), dried over sodium sulfate, and evaporated to give Candesartan cilexetil crude.

Example 4

Method of Deprotection Using p-Toluene Sulphonic Acid

A solution of cilexetil trityl candesartan (0.50 g, 0.59 mmol), PPTS (pyridine para-toluene sulphonic acid, 0.22 g, 0.88 mmol), dichloromethane (10 ml) and methanol (1 ml) was stirred at 25° C. to 27° C. for about 20 h. The reaction progress was monitored using thin layer chromatography (TLC monitoring). The reaction mixture was neutralized with a saturated solution of sodium bicarbonate. The dichloromethane was removed under reduced pressure, the residue was diluted with water (10 ml) and extracted with ethyl acetate (20 ml×2). The combined organic layers were washed with brine (10 ml×2), dried over sodium sulfate, and evaporated to give Candesartan cilexetil crude.

Example 5

Method of Deprotection Using Formic Acid

A solution of cilexetil trityl candesartan (2.0 g, 2.35 mmol), formic acid (2.16 g, 46.9 mmol), dichloromethane (8 ml) and methanol (4 ml) was stirred at 25° C. to 27° C. for about 5 h (TLC monitoring). The reaction mixture was neutralized with a saturated solution of sodium bicarbonate. The dichloromethane was removed under reduced pressure, the residue was diluted with water (10 ml) and extracted with ethyl acetate (20 ml×2). The combined organic layer was washed with brine (10 ml×2), dried over sodium sulfate and evaporated to give an oil (2.05 g) which was crystallized from tert-butyl methyl ether (TBME) (2.7 g) to give Candesartan cilexetil (0.95 g, 66.4%).

Example 6

Method of Deprotection Using Formic Acid

A solution of cilexetil trityl candesartan (1.0 g, 1.18 mmol) was dissolved in toluene (10 ml) at 50° C. to 55° C. followed by addition of formic acid (1.1 g, 23.88 mmol), and methanol (6 ml). The solution was heated to 50° C. to 55° C. for about 7 h. The reaction mixture was cooled to 20° C. to 25° C., pH adjusted to pH of 6.4 with 1 N NaOH, and extracted with ethyl acetate (20 ml×3). The combined organic layers were washed with brine (10 ml×2), dried over sodium sulfate and evaporated to give a semi-solid mass (0.79 g).

Example 7

Method of Deprotection Using Formic Acid

A solution of trityl candesartan cilexetil (30 g, 0.035 mol) in toluene (180 ml), methanol (180 ml), and formic acid (1.6 g, 0.035 mol) was refluxed for about 10 h. The reaction was monitored using HPLC. Thereafter, the solution volume was reduced by evaporation under reduced pressure (30 mbar) at a temperature of about 55° C. to 60° C. to obtain viscous oil (36.5 g). The oil was dissolved in a mixture of toluene: methanol (65.7 g:7.3 g), stirred at about 0° C. to 5° C. until crystallization started, and kept at 2° C. to 8° C. for about 20 hours. The solids were collected by filtration, washed on the filter with a mixture toluene/methanol (90:10 w/w, 15 g), and dried under reduced pressure (10–50 mm Hg) at a temperature of about 50° C. to 55° C. to yield candesartan cilexetil (16.88 g, 78.6%) as a white powder.

Example 8

Method of Deprotection Using Trifluoroacetic Acid

The protecting group (trityl) was removed using strong organic acids. Trifluoroacetic acid (0.1 ml, 1.3 eq.) was added at 20° C. to 25° C. to a stirred suspension of cilexetil trityl candesartan (1 g) in methanol (6 ml) and toluene (6 ml). After 50 min of stirring at 20° C. to 25° C. a solution formed. The solution was stirred at 20° C. to 25° C. for about an additional 6 h. Thereafter, the pH of the solution was adjusted to 6.4 with a saturated aqueous solution of sodium bicarbonate, the solution was diluted with brine (20 ml), and extracted with ethyl acetate (20 ml×2). The combined organic layers were washed with brine (10 ml), dried over sodium sulfate, filtered, and the volume reduced by evaporation to give a semi-solid mass crude candesartan cilexetil.

Alternatively, trichloroacetic acid may be used with this process.

Example 9

Method of Deprotection Using Trifluoroacetic Acid

Trifluoroacetic acid (0.17 g, 0.65 eq.) was added dropwise at a temperature of about 20° C. to about 25° C. to a stirred suspension of cilexetil trityl candesartan (2 g, 2.34 mmol) in toluene (12 ml) and methanol (12 ml). A solution formed after 1.5 h of stirring and the solution was stirred for about 20 h at a temperature of about 20° C. to about 25° C. Thereafter, the pH of the solution was adjusted to a pH 6.5 with a saturated solution of sodium bicarbonate, diluted with water (30 ml), and extracted with ethyl acetate (20 ml×4). The organic layers were collected and dried over sodium sulfate, filtered, and the solvent was removed by evaporation to yield semi-solid candesartan cilexetil.

Example 10

Deprotection Without Acid

Cilexetil trityl candesartan (5.0 g, 5.86 mmol) was dissolved at 60° C. in toluene (30 ml). Methanol (30 ml) was added and the solution was heated in an oil bath to 70° C. for about 19 h. The volume of the solution was reduced at 50° C. to 60° C. under reduced pressure to a weight of about 16 g and then cooled to −10° C. for about 48 h. The precipitated solids were collected by filtration, washed with cold methanol (MeOH at about 0° C. to 5° C.; 2 ml×2), dried on the filter for about 1 h to give crude candesartan cilexetil (3.1 g, 88.5%). The crude candesartan cilexetil was dissolved at reflux in methanol (23 ml), the solution was filtered under reduced pressure, and cooled under stirring in an ice bath for about 3 h. White solids were collected by filtration, washed with methanol (2.5 ml×3), and dried in the open air overnight to give candesartan cilexetil as a white solid (2.3 g, 74%) with 99.28% purity by HPLC.

Example 11

Deprotection Without Acid

Cilexetil trityl candesartan (20 g, 23 mmol) was dissolved at 60° C. in toluene (120 ml). Methanol (120 ml) was added and the solution was heated in an oil bath at about 75° C. to 80° C. for about 13 hours. The solution was reduced in volume by evaporation at 50° C. to 60° C. under reduced pressure to give a viscous residue (about 27 g) which was dissolved in methanol (60 ml) and the solvent removed by evaporation to dryness to give a foam (about 23 g). The foam was dissolved in methanol (about 40 g) at reflux temperature. The solution was then filtered under reduced pressure, cooled to 4° C. to obtain a solid and kept at this temperature for 12 to 15 hours.

The precipitated solids were collected by filtration, washed with the cold methanol at about 0° C. to 5° C. (20 ml×2) and dried at 50° C. under vacuum to give candesartan cilexetil (15.5 g). Trituration of candesartan cilexetil (1 g) with toluene (5 ml) at 25° C. to 27° C. during 1 h gave candesartan cilexetil (about 0.65 g).

Example 12

Deprotection Without Acid

A mixture of trityl candesartan cilexetil (20 g, 23.45 mmol), toluene (60 ml), methanol (60 ml), and water (1 ml)

was gently refluxed for about 12 h. The reaction was monitored by HPLC. The solution volume was reduced by evaporation under reduced pressure (30 mbar) at a temperature of about 55° C. 60° C. to obtain viscous oil of candesartan cilexetil as a residue (36.5 g).

Example 13

Deprotection without Acid

A mixture of trityl candesartan cilexetil (20 g, 23.45 mmol), toluene (60 ml), methanol (120 ml), and water (1 ml) was gently refluxed for about 5 h. The reaction progress was monitored by HPLC. The solution volume was reduced by evaporation under reduced pressure (30 mbar) at a temperature of about 55° C. to 60° C. to obtain viscous oil of candesartan cilexetil as a residue (36.5 g).

Example 14

Deprotection Without Acid

A mixture of trityl candesartan cilexetil (20 g, 23.45 mmol), methanol (200 ml), and water (1 ml) was gently refluxed for about 16–17 h. The reaction progress was monitored by HPLC. The solution volume was reduced by evaporation under reduced pressure (30 mbar) at a temperature of 55° C. to 60° C. to obtain viscous oil of candesartan cilexetil as a residue.

Example 15

Deprotection Without Acid

A solution of trityl candesartan c (TCS, 350 g, 410.3 mmol), toluene (1050 mL), methanol (2100 mL) and water (17.0 mL) was refluxed for about 2–4 h (HPLC control), the solvents were evaporated at 40–50° C./P<100 mbar to give a residue as a viscous oil, the residue was dissolved at 45–55° C. in a mixture of Toluene/Methanol (1041 g, 95:5, w/w) to give a clear solution.

The solution was cooled to (–5)–(20)° C. the solution was kept at this temperature for about 8–12 hr, the precipitated solids were filtered off, washed on the filter with cold Toluene (350 mL) to give a wet solid (295.8 g, 83.0%) 110 g of the wet solid were dried at 50° C./10 mbar for 2–6 hr to give a wet white solid (94 g (LOD=15–25%)). The wet white solid (43.75 g) was dissolved at 40–60° C. in Ethanol Absolute (215–363 mL 6–10V), the solution was filtered and returned to the reactor, then the solution was cooled to (–15)–(5)° C. and was kept at this temperature for about 2–24 hr. The precipitated solids were filtered off, washed with cold Ethanol Absolute (23–35 mL) to give wet solid which was dried at 50° C./10 mbar to constant weight to give cilexetil candesartan (21.5 g, 67%).

Example 16

Deprotection Without Acid

A suspension of cilexetil trityl candesartan (50.0 g, 58.62 mmol), water (2.64 g, 2.5 eq), and methanol (500 ml, 10 eq. by volume) was refluxed for about 16.5 h to obtain a clear solution. The solvents were removed by evaporation at 30 mbar and 40° C. to obtain a solid residue (51.7 g). The residue was dissolved at 60° C. in a mixture of toluene/methanol (95:5 w/w, 125 g), cooled to 20–23° C. and stirred for about 15 h. A precipitate appeared and was collected by filtration, washed with a cold (4° C.) mixture of toluene/methanol (95:5 w/w, 25 g), and dried for 2 h at 50° C. and 30 mbar to give a crude solid candesartan cilexetil (32.41 g, 90.5%), with 99.32% purity by HPLC.

Example 17

Deprotection Without Acid

A solution of Trityl Candesartan Cilexetil (100.0 g, 0.117 mol), Water (5.3 g), Toluene (600 mL) and Methanol (600 mL) was refluxed for about 10 h (HPLC in process control) and the solvents were evaporated at 60° C./30 mbar to obtain an oily residue. A part from the residue (6.84 g) was dissolved at 50° C. in a mixture of Toluene/Methanol 95:5 (w/w), (11.2 g). A solution was stirred for about 6 h at 2–8° C., the solids were filtered off, washed with a cold mixture of Toluene/Methanol 95:5 (w/w), (3.4 g) and dried at 60° C./30 mbar to the constant weight to give white solid (3.47 g, 86.8%), 99.15% pure by HPLC.

Example 18

Recrystallization in Methanol

The compound of Example 8 (5 g) was dissolved in methanol (25.0 g) at a temperature of about 18° C. to 23° C. to obtain a clear solution and upon which the solid precipitated to form a suspension. The suspension was stirred at 18° C. to 23° C. for about 60 h, the resulting solid was collected by filtration, washed with methanol (2.5 g), and dried under reduced pressure (10 mbar) at a temperature of about 50° C. to 55° C. until the solid had a constant weight to obtain candesartan cilexetil (4.2 g, 84%) as a white powder.

Example 19

Recrystallization in Methanol

The compound of Example 8 (2 g) was dissolved in methanol (6.0 g) at 50° C. to obtain a clear solution. The solution was cooled to about 18° C. to 23° C. until a precipitate began to form. Thereafter, the suspension was stirred at 18° C. to 23° C. for about 60 h, the solid was collected by filtration, washed with methanol (1.0 g), and dried under reduced pressure (10 mbar) at a temperature of 50° C. to 55° C. until the solid had a constant weight to obtain candesartan cilexetil (1.74 g, 87.0%) as a white powder.

Example 20

Recrystallization in Ethanol

The compound of Example 8 (5 g) was dissolved in ethanol (25.0 g) at 50° C. to obtain a clear solution. The solution was cooled to about 18° C. to 23° C., until a precipitate began to form. The suspension was stirred at 18° C. to 23° C. for about 60 h, the solid collected by filtration, washed with ethanol (2.5 g), and dried under reduced pressure (10 mbar) at a temperature of 50° C. to 55° C. until the solid had a constant weight to obtain candesartan cilexetil (4.17 g, 83.4%) as a white powder.

Example 21

Recrystallization in Ethanol

The compound of Example 1 (2 g) was dissolved in ethanol (25.0 g) at 60° C. to obtain a clear solution. The solution was cooled to about 18° C. to 23° C., until a precipitate began to form. The suspension was stirred at 18° C. to 23° C. for about 60 h, the solid was collected by filtration, washed with ethanol (1.0 g), and dried under reduced pressure (10 mbar) at a temperature of 50° C. to 55° C. until the solid had a constant weight to obtain candesartan cilexetil (1.68 g, 84.0%) as a white powder.

What is claimed is:

1. A process for preparing cilexetil trityl candesartan comprising:
   reacting trityl candesartan, cilexetil halide and at least one base in a low boiling organic solvent to form cilexetil trityl candesartan; and
   isolating cilexetil trityl candesartan.

2. The process according to claim 1, wherein the reaction is conducted in the presence of a phase transfer catalyst.

3. The process according to claim 1, wherein the cilexetil halide is cilexetil chloride.

4. The process according to claim 1, wherein the low boiling organic solvent has a boiling point of less than about 140° C.

5. The process according to claim 4, wherein the low boiling organic solvent has a boiling point of less than about 120° C.

6. The process according to claim 1, wherein the low boiling organic solvent is at least one of an aliphatic solvent, aromatic solvent, or ether.

7. The process according to claim 1, wherein the low boiling organic solvent is acetonitrile or toluene.

8. The process according to claim 1, wherein the low boiling organic solvent is a pharmaceutically acceptable low boiling point organic solvent having a boiling point from about 140° C. to about 70° C.

9. The process according to claim 8, wherein the low boiling organic solvent is a pharmaceutically acceptable low boiling point organic solvent having a boiling point from about 120° C. to about 80° C.

10. The process according to claim 1, wherein the base is selected from the group consisting of an inorganic base.

11. The process according to claim 10, wherein the base is at least one of lithium hydroxide, sodium hydroxide, potassium hydroxide, cesium hydroxide, lithium carbonate, sodium carbonate, potassium carbonate, cesium carbonate, lithium hydrogen carbonate, sodium hydrogen carbonate, potassium hydrogen carbonate, or silver carbonate.

12. The process according to claim 1, wherein the base is selected from the group consisting of an organic base.

13. The process according to claim 12, wherein the base is at least one of triethylamine, diisopropylethylamine, pyridine, N,N-dimethylaniline, N-methyl-morpholine, 4-dimethylaminopyridine, 1,5-diazabicyclo-[4.3.0]non-5-ene (DBN), 1,8-diazabicyclo[5.4.0]undec-7-ene (DBU), or 1,4-diazabicyclo[2.2.2]octane (DABCO).

14. The process according to claim 2, wherein the phase transfer catalyst is at least one of tetrabutylammonium bromide, TEBA, tetrabutylammonium hydrogensulfate, tricaprylylmethylammonium chloride, benzyltriethylammonium chloride, cetyltrimethylammonium bromide, cetylpyridinium bromide, N-benzylquininium chloride, tetra-n-butylammonium chloride, tetra-n-butylammonium hydroxide, tetra-n-butylammonium iodide, tetra-ethylammonium chloride, benzyltributylammonium bromide, benzyltriethylammonium bromide, hexadecyltriethylammonium chloride, tetramethylammonium chloride, hexadecyltrimethyl ammonium chloride, or octyltrimethylammonium chloride.

15. The process according to claim 2, wherein the phase transfer catalyst is at least one of tetrabutylammonium bromide, TEBA, tricaprylylmethylammonium chloride, or tetrabutylammonium hydrogensulfate.

16. The process according to claim 1, wherein the process is carried out at a reaction temperature of about 25° C. to about 110° C.

17. The process according to claim 16, wherein the process is carried out at a reaction temperature of about 40° C. to about 90° C.

18. A process for preparing cilexetil trityl candesartan comprising:
   reacting trityl candesartan, cilexetil halide and DMF at a temperature of about 50° C. to about 55° C. to form cilexetil trityl candesartan; and
   isolating cilexetil trityl candesartan.

19. The process according to claim 18, wherein the reaction is conducted in the presence of a phase transfer catalyst.

20. The process according to claim 18, wherein the cilexetil halide is cilexetil chloride.

21. The process according to claim 18, wherein the base is selected from the group consisting of an inorganic base.

22. The process according to claim 18, wherein the base is selected from the group consisting of an organic base.

23. A process for preparing cilexetil trityl candesartan comprising:
   mixing trityl candesartan, cilexetil chloride, and potassium carbonate in acetonitrile;
   heating the reaction to the reflux temperature of acetonitrile to form cilexetil trityl candesartan; and
   isolating cilexetil trityl candesartan.

24. The process according to claim 23, wherein the reaction is heated to 40° C. for about 8 h.

* * * * *

UNITED STATES PATENT AND TRADEMARK OFFICE
CERTIFICATE OF CORRECTION

PATENT NO. : 7,098,342 B2  
APPLICATION NO. : 10/968710  
DATED : August 29, 2006  
INVENTOR(S) : Etinger et al.

Page 1 of 1

It is certified that error appears in the above-identified patent and that said Letters Patent is hereby corrected as shown below:

Column 4, line 43, change "tricaprylylmethylammonium chloride" to --tricaprylmethylammonium chloride--

Column 4, line 45-46, change "tricaprylylmethylammonium chloride" to --tricaprylmethylammonium chloride--

Column 14, line 7-8, change "tricaprylylmethylammonium chloride" to --tricaprylmethylammonium chloride--

Column 14, line 20, change "tricaprylylmethylammonium chloride" to --tricaprylmethylammonium chloride--

Signed and Sealed this

Twenty-sixth Day of May, 2009

JOHN DOLL  
*Acting Director of the United States Patent and Trademark Office*